(12) United States Patent
Mitter (10) Patent No.: US 7,077,004 B2
(45) Date of Patent: Jul. 18, 2006

(54) METHOD AND DEVICE FOR MEASURING HUMIDITY

(75) Inventor: Helmut Mitter, Hellmonsocdt (AT)

(73) Assignee: E+E Elektronik Ges.m.b.H, Engerwitzdorf (AT)

( * ) Notice: Subject to any disclaimer, the term of this patent is extended or adjusted under 35 U.S.C. 154(b) by 66 days.

(21) Appl. No.: 10/909,479

(22) Filed: Aug. 2, 2004

(65) Prior Publication Data

US 2005/0028588 A1 Feb. 10, 2005

(30) Foreign Application Priority Data

Aug. 2, 2003 (DE) ............................. 103 35 553

(51) Int. Cl.
*G01N 19/10* (2006.01)
*G01R 27/26* (2006.01)

(52) U.S. Cl. ............... 73/335.04; 73/29.01; 73/29.02; 73/29.05; 73/31.05; 73/335.02; 73/335.05

(58) Field of Classification Search .............. 73/29.01, 73/29.02, 29.05, 31.05, 335.02–335.05
See application file for complete search history.

(56) References Cited

U.S. PATENT DOCUMENTS

| 3,810,389 | A | | 5/1974 | Jason ................... 73/335.03 |
| 4,203,087 | A | * | 5/1980 | Kovac et al. ............ 338/35 |
| 4,277,742 | A | * | 7/1981 | Kovac et al. ............ 324/689 |
| 4,677,416 | A | * | 6/1987 | Nishimoto et al. ........ 338/35 |
| 4,794,323 | A | * | 12/1988 | Zhou et al. ............. 324/71.5 |
| 5,533,393 | A | * | 7/1996 | Bonne et al. ........... 73/335.02 |
| 5,656,928 | A | * | 8/1997 | Suzuki et al. ........... 324/71.1 |
| 5,792,938 | A | * | 8/1998 | Gokhfeld ............... 73/29.02 |
| 5,814,726 | A | | 9/1998 | Mitter .................. 73/335.04 |
| 6,073,480 | A | * | 6/2000 | Gokhfeld ............... 73/29.02 |
| 6,079,121 | A | * | 6/2000 | Khadkikar et al. ........ 34/528 |
| 6,356,087 | B1 | * | 3/2002 | Wallrafen ............... 324/664 |
| 2002/0092525 | A1 | * | 7/2002 | Rump et al. ........... 128/205.23 |
| 2004/0012912 | A1 | * | 1/2004 | Rombach .............. 361/321.6 |

FOREIGN PATENT DOCUMENTS

| DE | 197 29 697 | 2/1999 |
| EP | 0 801 302 | 10/1997 |
| GB | 2 011 093 | 7/1979 |
| GB | 2 047 431 | 11/1980 |
| GB | 2 323 928 | 10/1998 |
| JP | 6-33122 | 1/1994 |
| JP | 7-146273 | 6/1995 |

* cited by examiner

*Primary Examiner*—Hezron Williams
*Assistant Examiner*—David A. Rogers
(74) *Attorney, Agent, or Firm*—Kenyon & Kenyon LLP (57) ABSTRACT

A method and a device for measuring humidity may be suitable for determining the relative humidity in the high-humidity range. The device includes a sensor device, as well as a circuit connected to the same. The sensor device includes a capacitive humidity-sensor element, a temperature-sensor element, and a heating element, the humidity-sensor element being heated in at least one part of the humidity-measuring range. The ambient temperature is further ascertained by the circuit, from the heating power required in the heating mode, as well as from the measured, local sensor device temperature, in order to further determine the relative humidity.

21 Claims, 10 Drawing Sheets

METHOD AND DEVICE FOR MEASURING HUMIDITY

CROSS-REFERENCE TO RELATED APPLICATIONS

The present application claims priority to Application No. 103 35 553.7, filed in the Federal Republic of Germany on Aug. 2, 2003, which is expressly incorporated herein in its entirety by reference thereto.

FIELD OF THE INVENTION

The present invention relates to a method and a device for measuring humidity.

BACKGROUND INFORMATION

When measuring relative humidity with the aid of sensor devices having capacitive humidity sensor elements, measuring errors often occur in the high-humidity range (rH>95%). In particular, relative humidity readings that are too high are sometimes measured in this connection. A number of causes may be responsible for this effect, for example, the general saturation behavior of the humidity-sensor elements, the beginning condensation and the resulting short-circuits at the contacts of the humidity-sensor elements, etc.

European Published Patent Application 0 801 302 describes a method and a device for determining the absolute humidity, where the device is operated in a heating mode at or above a particular humidity limit value. In heating mode, the temperature of the utilized capacitive humidity-sensor element is adjusted to a constant humidity-sensor capacitance. This occurs in this measuring range, i.e., in the high humidity range, by suitably heating the humidity-sensor element with the aid of a temperature-sensor element, which is situated adjacent to the humidity-sensor element in the sensor device. In the high-humidity range, the specific, absolute humidity may then be ascertained from the measured heating current and the known capacitance of the humidity-sensor element. If necessary, in order to still be able to ascertain specific, relative humidity rH in addition to the absolute humidity, where the relative humidity represents the desired quantity to be measured in many different applications, knowledge of ambient temperature $T_a$ is also required. This means that a further component in the form of a temperature sensor is necessary for measuring ambient temperature $T_a$. This may result in an increased total expenditure within a conventional device, when, in addition to or in place of the absolute humidity, relative humidity rH is also needed as a measured quantity.

SUMMARY

It is an aspect of the present invention to provide a method and a device for measuring humidity, in order to additionally allow a reliable determination of the relative humidity in the high-humidity range with as little expenditure as possible.

Example embodiments of the method and device according to the present invention are described herein.

An example embodiment of the present invention may provide for the ambient temperature not to be ascertained with the aid of a separate temperature-sensor element, but rather to be derived from the heating power necessary in heating mode and the local sensor device temperature. The specific measuring current through the utilized heating element is used as a measured variable for determining the heating power.

Therefore, an example embodiment of the present invention may eliminate the need for a separate temperature-sensor element to determine the ambient temperature. At the same time, the heating mode in at least the high-humidity range may ensure that a correct determination of the relative humidity results.

Various design options are possible. Thus, only a capacitive humidity-sensor element and a temperature-sensor element may be provided in a minimal configuration of a suitable sensor device of the device according to an example embodiment of the present invention, the temperature-sensor element being simultaneously used for heating, i.e., as a heating element. In general, it may also be provided, however, that the functionality of the temperature-sensor element and the heating element be distributed to two separate components in the sensor device. There may be, therefore, a number of options regarding the hardware-related design of the sensor device.

Furthermore, there may be different options with regard to the arrangement of the heating mode. Thus, it may be provided, for instance, as in the case of the above-mentioned document, European Published Patent Application No. 0 801 302, that the humidity-sensor element is adjustably heated at or above a particular humidity limit value, so that a constant capacitance of the humidity-sensor element may always result in this measuring range. As an alternative, it is, however, also possible to heat the humidity-sensor element at or above a selected, humidity limit value, using a heating current that linearly increases with the relative humidity in this measuring range. Furthermore, it may also be possible to heat the humidity-sensor element in the entire measuring range, which, in this case, may also be performed in an unregulated manner.

The different design variants of the sensor device may be combined with the different variants of the method in a large variety of manners.

According to an example embodiment of the present invention, a method for measuring humidity by a sensor device, which includes a capacitive humidity-sensor element, a temperature-sensor element and a heating element, includes: heating the humidity-sensor element in at least a part of a humidity-measuring range; ascertaining an ambient temperature by a circuit from a heating power required in the heating step and from a measured local sensor device temperature; and determining the relative humidity from the ambient temperature and the local sensor device temperature.

The relative humidity may be in a high-humidity range.

The method may include entering a heating mode at or above a predetermined humidity limit value.

The humidity-sensor element may be heated in the heating mode in a regulated manner to provide a constant capacitance of the humidity-sensor element.

The humidity-sensor element may be heated in the heating mode by a heating current that increases linearly with the relative humidity.

The humidity-sensor element may be heated in the heating step over an entire humidity-measuring range.

The temperature-sensor element and the heating element may be integral.

The method may include determining an excess temperature of the heating element resulting from the heating power, the ambient temperature ascertained in the ambient temperature ascertaining step from the heating power and the local sensor device temperature in accordance with the relationship $T_a \infty T_s - T_x$, $T_a$ representing the ambient temperature, $T_s$ representing the local sensor device temperature and $T_x$ representing the excess temperature.

The excess temperature determining step may include determining a corresponding measurement current by the temperature-sensor element, the excess temperature determined in the determining step in accordance with the relationship $T_x = R*TK*I^2*EK$, $T_x$, representing the excess temperature, R representing a measured resistance of the temperature-sensor element at the temperature, TK representing a temperature coefficient of the temperature-sensor element, I representing the measurement current through the temperature-sensor element and EK representing a characteristic heating coefficient of the temperature-sensor element.

The humidity-sensor element heating step, the ambient temperature ascertaining step and the relative humidity determining step may be performed by the circuit post-connected to the sensor device.

The circuit may be configured to output the ambient temperature and the relative humidity for further processing.

According to an example embodiment of the present invention, a device for measuring humidity includes: a sensor device including a capacitive humidity-sensor element, a temperature-sensor element and a heating element; and circuit configured to heat the humidity-sensor element in at least a part of a humidity-measurement range, and configured to ascertain an ambient temperature from a heating power required in a heating mode and from a measured local sensor device temperature to determine the relative humidity.

The device may be configured to determine relative humidity in a high-humidity range.

The circuit may be configured to operate the sensor device in the heating mode at or above a predetermined humidity limit value.

The circuit may be configured to heat, in the heating mode, the humidity-sensor element in a regulated manner to result in a constant capacitance of the humidity-sensor element.

The circuit may be configured to heat, in the heating mode, the humidity-sensor element by a heating current that increases linearly with the relative humidity.

The circuit may be configured to heat the humidity-sensor element over an entire humidity-measuring range.

The temperature-sensor element and the heating element may be integral.

The temperature-sensor element may include at least one resistor element, the sensor device may include a carrier substrate, and the capacitive humidity-sensor element and the at lest one resistor element may be arranged on the carrier substrate. The at least one resistor element may be further arranged as the heating element.

The circuit may be post-connected to the sensor device and may include at least one microprocessor configured to heat the humidity-sensor element, to perform signal processing and to provide output signals.

Other aspects of the present invention as well as details pertaining thereto are derived from the following description of exemplary embodiments with reference to the appended Figures.

DETAILED DESCRIPTION

Figure 1:
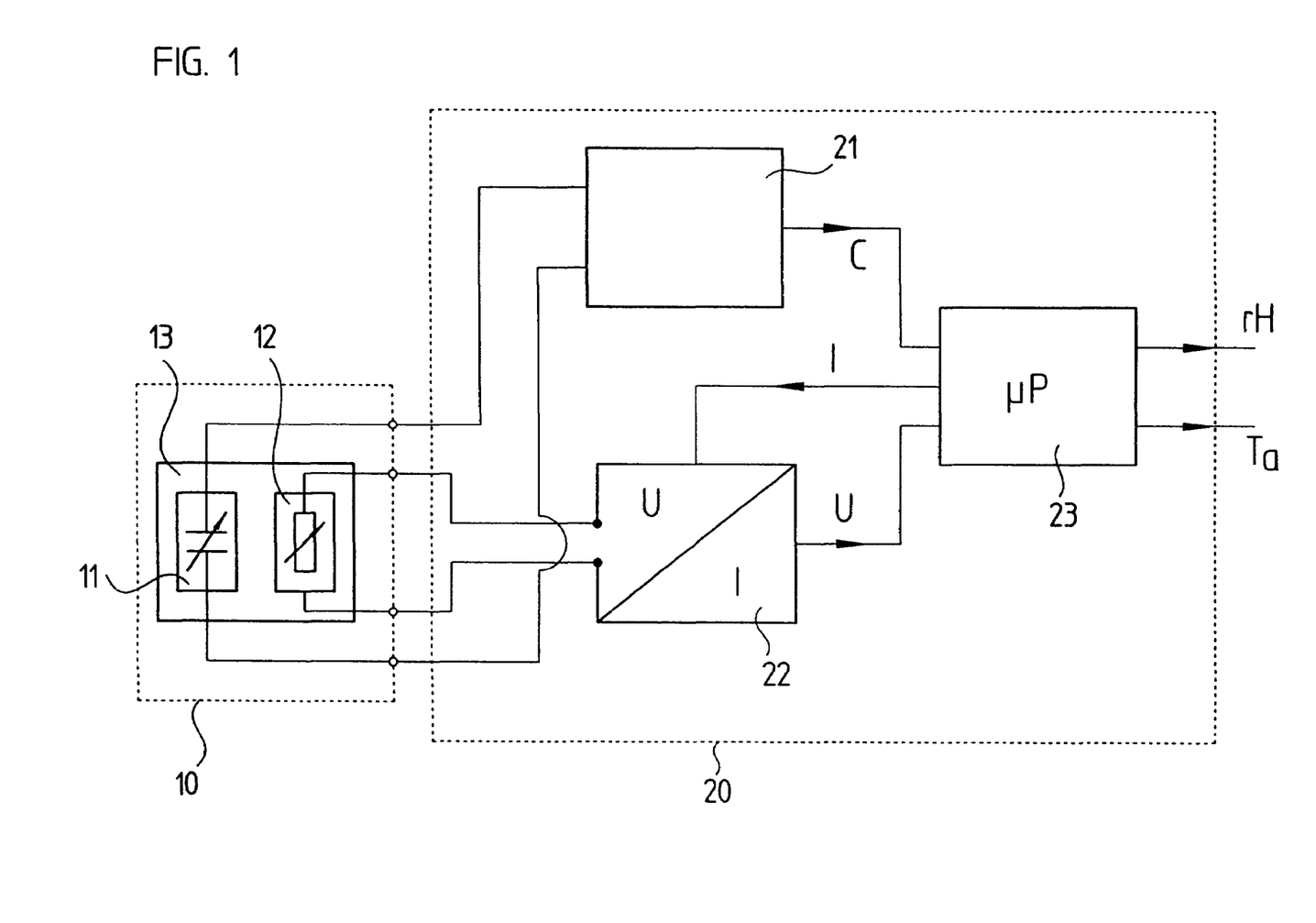
FIG. 1 is a schematic block diagram of an exemplary embodiment of a device according to the present invention.

FIG. 1 is a block diagram of an example embodiment of a device according to the present invention. The represented components are briefly explained, while the method of an example embodiment of the present invention and a device suitable for implementing it, as well as different exemplary embodiment options of the same, are subsequently described in detail with reference to FIGS. 2a to 2c, 3a to 3c, and 4a to 4c.

With sensor-device 10 and a circuit 20, the device of an example embodiment of the present invention includes two functional units or functional blocks. In the represented example, sensor device 10 is provided with a humidity-sensor element 11 and a temperature-sensor element 12, which are arranged on a common carrier substrate 13. Humidity-sensor element 11 may take the form of a capacitive humidity-sensor element made up of two planar electrodes, between which, e.g., a polymer in the form of a dielectric is arranged, the capacitance of the polymer changing as a function of humidity. Temperature-sensor element 12 may take the form of a resistive sensor element and may include a resistor having a linear temperature-resistance characteristic, in order to determine the temperature of the sensor-device from the resistance measurement, e.g., in a conventional manner. The two sensor elements 11, 12 may be arranged on a carrier substrate 13, which may take the form of a thin glass wafer.

In the illustrated exemplary embodiment, temperature-sensor element 12 of sensor device 10 may also function as a heating element, in order to heat the sensor device in a selected measuring range during the measuring operation explained below in detail. In other words, the block diagram illustrated in FIG. 1 therefore represents a minimum configuration of a device according to an example embodiment of the present invention.

In an example embodiment, a so-called sandwich construction may be provided for this, the sandwich construction including a capacitive humidity sensor on a glass carrier substrate, as well as a conventional Pt temperature sensor on a ceramic carrier substrate. The back sides of the two carrier substrates may be bonded to each other in a thermally conductive manner.

In principle, it may also be provided that, in addition to temperature-sensor element 12, a separate heating element is used for sensor device 10. For example, this heating element may take the form of a resistor and my be arranged on carrier substrate 13. The temperature-sensor element may always be operated with a small measuring current, and the temperature measurement may be taken in the meantime. The separate heating element may be operated with a specific heating current as a function of the operating state, and therefore, it may only assume the function of heating.

Circuit 20, of which certain functional blocks are schematically illustrated in FIG. 1, are post-connected to sensor device 10. Thus, reference numeral 21 designates a capacitance-determination unit, which may be in the form of a capacitance-measuring circuit, is connected to capacitive, humidity-sensor element 11, and may be used in a conventional manner to measure the specific capacitance, of which the respective humidity is a specific function. In each instance, ascertained capacitance C is transmitted from capacitance-determination unit 21 to a post-connected microprocessor 23 for further processing.

Furthermore, on the side of circuit 20, a unit, which is connected to resistive temperature-sensor element 12 or heating element, is designated by reference numeral 22. In this connection, unit 22 may take the form of a regulated current source for supplying the heating element with a heating current, and may also allow the voltage across resistive temperature-sensor element 12 to be measured, in order to consequently ascertain the temperature of the sensor device. In order to selectively regulate the heating current via the input of a setpoint heating current I, or to transfer ascertained voltage value U for reasons of temperature measurement, unit 22 is also connected to post-connected microprocessor 23.

Consequently, microprocessor 23 controls unit 22 for selecting a heating current, processes the different measuring data in the subsequently described manner, and provides output-side signals regarding ambient temperature $T_a$ and relative humidity rH. These may then be processed further in an application-specific manner in an evaluation unit.

Figure 2A:
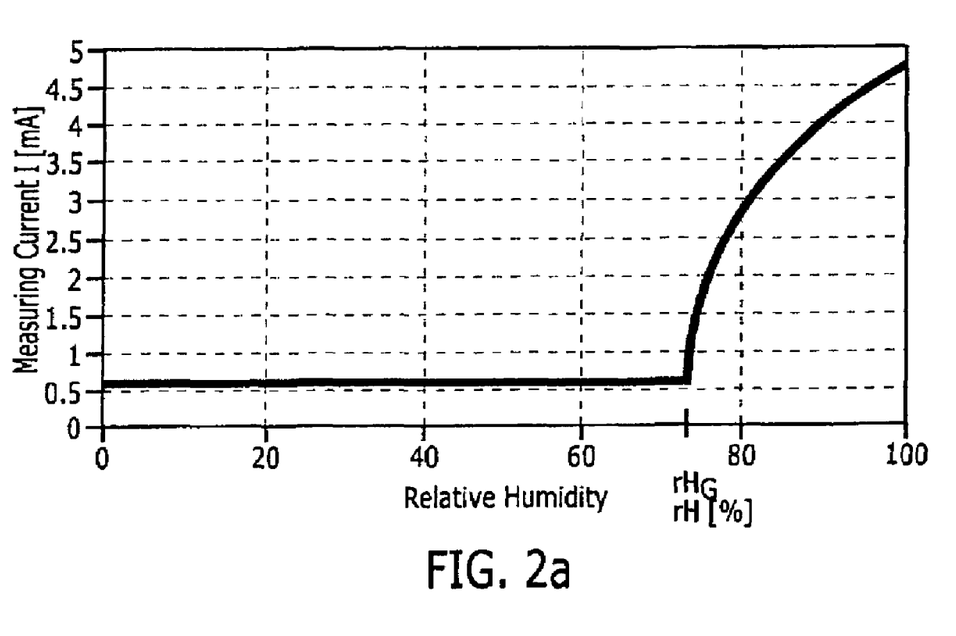
FIGS. 2a to 2c are various diagrams for explaining an example embodiment of a method according to the present invention.
Figure 2B:
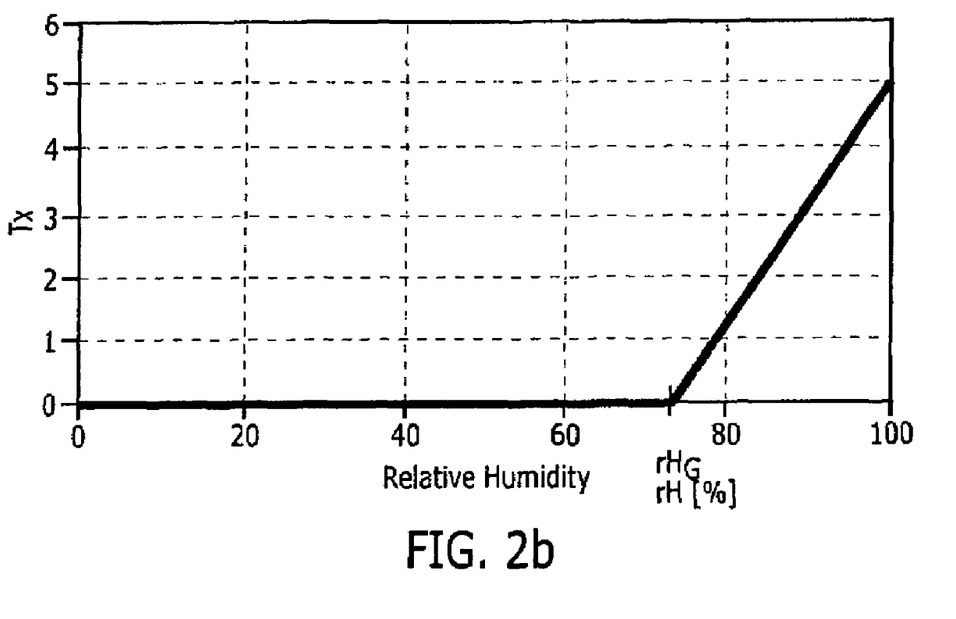
Figure 2C:
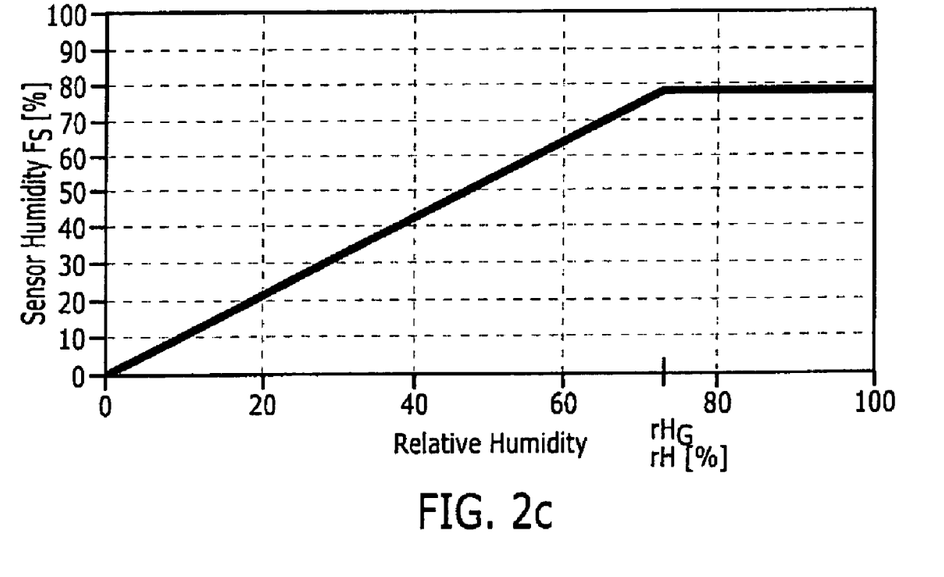

Referring to FIGS. 2a to 2c, an example embodiment of a method according to the present invention is described in detail with reference to FIG. 1. In the method, it is provided that the device is operated in a heating mode at or above a specified humidity limit value $rH_G$, i.e., the sensor device is heated by the heating element. The heating is such that the humidity-sensor element is adjustably heated in such a manner that a constant capacitance of the humidity-sensor element results in the heating mode. This occurs with increasing relative humidity rH, in that the utilized heating element correspondingly increases heating current $I_H$ in a regulated manner. In the case in which a combined temperature sensor and heating element is used, required heating current $I_H$ also corresponds to specific measuring current $I_M$, i.e., $I_H=I_M=I$, so that, in this case, only heating current or measuring current I is subsequently mentioned.

In the present example embodiment, a relative humidity $rH_G$ of 75% is provided as humidity limit value $rH_G$, at or above which the device operates in the regulated heating mode. In FIG. 2a, which represents the curve of measuring current I versus relative humidity rH, it is illustrated how heating current I, which remains constant up to a humidity limit value $rH_G$ of 75%, is then increased in a selective or regulated manner, in order to ensure a constant capacitance C of the humidity-sensor element.

In order to be able to determine desired ambient temperature $T_a$, as well, without a further sensor element, an example embodiment of the present invention may utilize the fact that, in heating mode, the heating power to be provided for the temperature sensor or the heating element and excess temperature $T_x$ resulting from it are proportional to the temperature difference between sensor device temperature $T_s$ and ambient temperature $T_a$. Consequently, ambient temperature $T_a$ is further ascertained by the circuit, from the heating power required in the heating mode, as well as from measured, local sensor device temperature $T_s$, in order to finally determine relative humidity rH. The following equation applies:

$$T_a=T_s-T_x \qquad \text{(equ. 1)}$$

in which $T_a$ represents ambient temperature, $T_s$ represents measured sensor device temperature, and $T_x$ represent excess temperature of the heating element, resulting from the applied heating power in the heating mode.

FIG. 2b illustrates the relationship between excess temperature $T_x$ of the heating element and the relative humidity. It is apparent that the resulting excess temperature increases at or above humidity limit value $rH_G$ (and the start of the heating mode, i.e., the temperature-sensor element heats up due to flowing heating current I.

FIG. 2c illustrates sensor humidity $F_s$ plotted versus relative humidity rH. In this example embodiment of the method according to the present invention, it is apparent that, during heating mode, sensor humidity $F_s$ is adjusted to a constant value of 75% at or above humidity limit value $rH_G$, i.e., capacitance C of the utilized, capacitive humidity-sensor element is adjusted to be constant.

Using an example, a detailed explanation follows as to how ambient temperature $T_a$ and, from this, the ultimately desired relative humidity rH in, e.g., the high-humidity range may be ascertained on the basis of equation (1) and the different measured quantities ascertained.

In this connection, one starts out from a conventional resistive temperature-sensor element, e.g. a Pt1000 element, the temperature-resistance characteristic of which may be linearly approximated by the following function:

$$R=R_s*(1+TK*T) \qquad \text{(equ. 2.1)}$$

in which R represents temperature-sensor resistance in Ω at temperature T in ° C., $R_s$ represents temperature-sensor resistance in Ω at 0° C., TK represents temperature coefficient in ppm/° C., and T represents measured temperature.

Measured temperature T is yielded from temperature-sensor resistance R according to the equation:

$$T=(R/R_s-1)/TK \qquad \text{(equ. 2.2)}$$

Values typical for a Pt1000 temperature-sensor element are:

$$R_s=1000\Omega$$

$$TK=3850 \text{ ppm}/° \text{C.}=0.00385 \text{ 1}/° \text{C.}$$

At an ambient temperature $T_a=23°$ C., one obtains, for example, a temperature-sensor resistance R=1088.55 Ohm.

Resistance value R of the temperature-sensor element may be determine using a current/voltage measurement. In a normal case, measuring current I is selected to be so low, that no significant warming occurs due to the power loss at the temperature-sensor element. In the case of a measurement current of, e.g., I=700 µA, the result is a measurement voltage U=0.761985 V at 23° C.

In actuality, a measurement using the low current of I=700 µA already produces a power loss of P=0.533 mW, which already results in self-heating or an excess temperature $T_x$ of approximately 0.1° C., given a typical characteristic heating coefficient EK=200° C./W. However, in conventional humidity-measuring systems, this may be mostly neglected or else systematically calibrated away.

If the self-heating of the temperature-sensor element caused by the measurement current is considered, then an additional term for the resulting self-heating may be introduced into equ. (2.1). At an ambient temperature $T_a$, resistance R of the temperature sensor is calculated as follows:

$$R=R_s*(1+TK*(T_a+T_x)) \qquad \text{(equ. 2.3)}$$

in which R represents temperature-sensor resistance in Ω at temperature T in ° C., $R_s$ represents temperature-sensor resistance in Ω at 0° C., TK represents temperature coefficient in ppm/° C., $T_a$ represents ambient temperature in ° C., and $T_x$ represents excess temperature of the temperature-sensor element in ° C.

Excess temperature $T_x$ of the temperature-sensor element is yielded from the different measured quantities as follows:

$$T_x = P*EK = U*I*EK = I^2*R*EK \quad \text{(equ. 2.4)}$$

in which P represents heating power in W, EK represents characteristic heating coefficient of the temperature-sensor element in ° C./W, U represents measurement voltage in V, I represents measurement current in A, and R represents temperature-sensor resistance in Ω.

For its part, resulting excess temperature $T_x$ is again a function of temperature-sensor resistance R, so that the insertion of equation 2.4 into equation 2.3 and appropriate reforming yields:

$$R = R_S*(1 + TK*(T_a + I^2*R*EK)) \quad \text{(equ. 2.5)}$$

$$= R_S*(1 + TK*T_a) + (R_S*TK*I^2*R*EK)$$

or $$R*(1 - R_S*TK*I^2*EK) = R_S*(1 + TK*T_a) \quad \text{(equ. 2.5')}$$

Temperature-sensor resistance R at ambient temperature $T_a$ is obtained from equation (2.5') as follows:

$$R = (R_s*(1+TK*T_a))/(1-R_s*TK*I^2*EK) \quad \text{(equ. 2.6)}$$

Conversely, desired ambient temperature $T_s$ may be determined from the measured quantity of measurement current I and characteristic heating coefficient EK from equation 2.6, by solving the equation for $T_a$ as follows:

$$T_a = ((R/R_S)*(1 - R_S*TK*I^2*EK) - 1)*1/TK \quad \text{(equ. 2.7)}$$

or $$T_a = (((R/R_S) - 1)*1/TK) - \quad \text{(equ. 2.7')}$$

$$((R/R_S)*(1/TK)*R_S*TK*I^2*EK)$$

$$= (((R/R_S) - 1)*1/TK) - (R*TK*I^2*EK)$$

$$= T_S - T_{\ddot{a}}$$

Therefore, first term $T_s$ in equation 2.7 indicates the temperature of the temperature-sensor element, how it is calculated from measured resistance R. On the other hand, the second, negative term indicates excess temperature $T_x$, which results from the power loss at resistor R at measurement current I.

The determination of ambient temperature $T_s$ on the basis of the derived equations is explained below with reference to an example. In this case, characteristic heating coefficient EK of the temperature-sensor element is assumed to be 200° C./w, and prevailing ambient temperature $T_a$ is assumed to be 23° C.

Above a humidity limit value $rH_G$ of 75%, measurement current I is increased to 5 mA, which causes the sensor device to heat up by approximately 5° C. The use of the above equations produces the following exact values:
  ascertained measurement voltage U=5.44275 V
  utilized measurement current I=5 mA
  =>R=1109.92Ω

Determined resistance R than yields a temperature of the temperature-sensor element $T_s$=28.55° C.

From equation 2.4, resistance value R=1109.92 Ω, measurement current I=5 mA, and specified characteristic heating coefficient EK=0.2° C./mW yield an excess temperature $T_x$=5.55° C.

Equation (1), i.e., $T_a = T_s - T_x$, then yields (correct) ambient temperature $T_a$=23° C.

Consequently, ambient temperature $T_a$ may be determined according to an example embodiment of the present invention in the above-mentioned manner, and may be used for ascertaining desired relative humidity rH. This is explained in the following.

Relative humidity rH is given as the ratio of current water-vapor partial pressure e to maximum possible saturation vapor pressure $e_w$ at temperature $T_a$, in %:

$$rH = e/e_w*100\% \quad \text{(equ. 3)}$$

Water-vapor partial pressure e is independent of the local gas temperature and may be plotted versus dew point $T_d$, using, for example, the Magnus formulas;

$$e = A*\exp(m*T_d/(T_n+T_d)) \quad \text{(equ. 4)}$$

where the (Magnus) parameters are A=6.112, m=17.62, and $T_n$=243.12.

Saturation humidity $e_w$, at a temperature $T_a$ may be correspondingly calculated according to:

$$e_w = A*\exp(m*T_d/(T_n+T_a)) \quad \text{(equ. 5)}$$

Water-vapor partial pressure e is theoretically independent of the gas temperature, as long as no condensation occurs. Accordingly, the dew point is defined as the temperature to which a humid gas (humid air) must be cooled for condensation to occur.

In particular, water-vapor partial pressure e and, therefore, $T_d$ are also independent of the local temperature at the humidity-sensor element. The local relative humidity changes when a humidity-sensor element (according to an example embodiment of the present invention) heats up, since the heating also causes the local saturation vapor pressure at the humidity-sensor element to change.

The following definitions are used in the further course of the description:

$$rH = e/e_w*100\% \quad \text{(equ. 6.1)}$$

$$rHs = e/e_{w.s}*100\% \quad \text{(equ. 6.2)}$$

$$e_w = A*\exp(m*T_a/(T_n+T_a)) \quad \text{(equ. 6.3)}$$

$$e_{w.s} = A*\exp(m*T_s/(T_n+T_s)) \quad \text{(equ. 6.4)}$$

in which rH represents relative humidity of the specific gas, $rH_s$ represents relative humidity at the location of the sensor, $e_w$ represents saturation vapor pressure at ambient temperature $T_a$, and $e_{w.s}$ represents saturation vapor pressure at sensor temperature $T_s$.

By measuring sensor temperature $T_s$ and relative humidity $rH_s$ at the location of the sensor, water-vapor partial pressure e and dew point $T_d$ may therefore be calculated as follows:

$$e_{w.s} = A*\exp(m*T_s/(T_n+T_s))$$

$$e = rH_s*e_{w.s}/100 \quad \text{(equ. 6.5)}$$

$$T_d = T_n*ln(e/A)/(m*ln(e/A)) \quad \text{(equ. 6.6)}$$

The determination of ambient temperature $T_a$ according to an example embodiment of the present invention allows actual atmospheric humidity rH to be calculated, using saturation vapor pressure $e_w$ at ambient temperature $T_a$.

$$e_w = A \ast \exp(m \ast T_a/(T_n+T_a)) \quad \text{(equ. 6.3)}$$

$$rH = e/e_w \ast 100\% \quad \text{(equ. 3)}$$

In the device according to an example embodiment of the present invention, the explained steps for ascertaining the ambient temperature and relative humidity rH from the different measured quantities are executed by the circuit and its above-mentioned functional units. That is, the circuit is appropriately designed to further ascertain the ambient temperature from the heating power necessary in heating mode and the measured, local sensor device temperature, in order to ultimately determine the relative humidity. On the output side, the circuit provides, for example, both the ascertained value for relative humidity rH and ascertained ambient temperature $T_a$ for further processing.

As an alternative to the explained method illustrated in FIGS. 2a to 2c, in each of which an adjustment is made in heating mode to a constant capacitance of the humidity-sensor element at or above humidity limit value $rH_G$, alternative variants of the heating mode are also possible. In principle, however, nothing in the manner of determining the ambient temperature changes in these cases, i.e., in these alternative methods, the ambient temperature is ultimately determined from the heating power required in heating mode and the measured sensor device temperature, as well, without a separate, required temperature-sensor element.

Figure 3A:
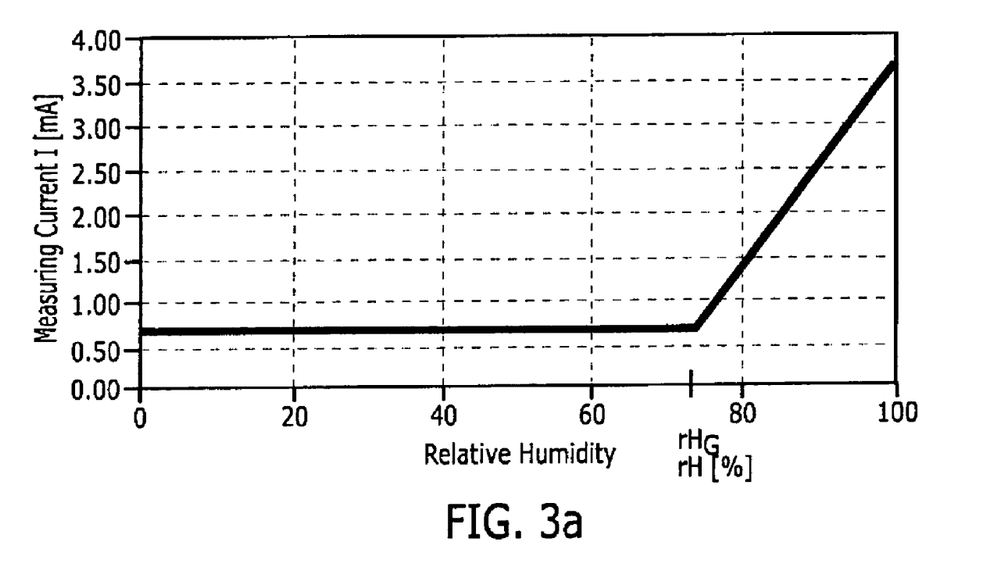
FIGS. 3a to 3c are various diagrams for explaining an example embodiment of the method according to the present invention.
Figure 3B:
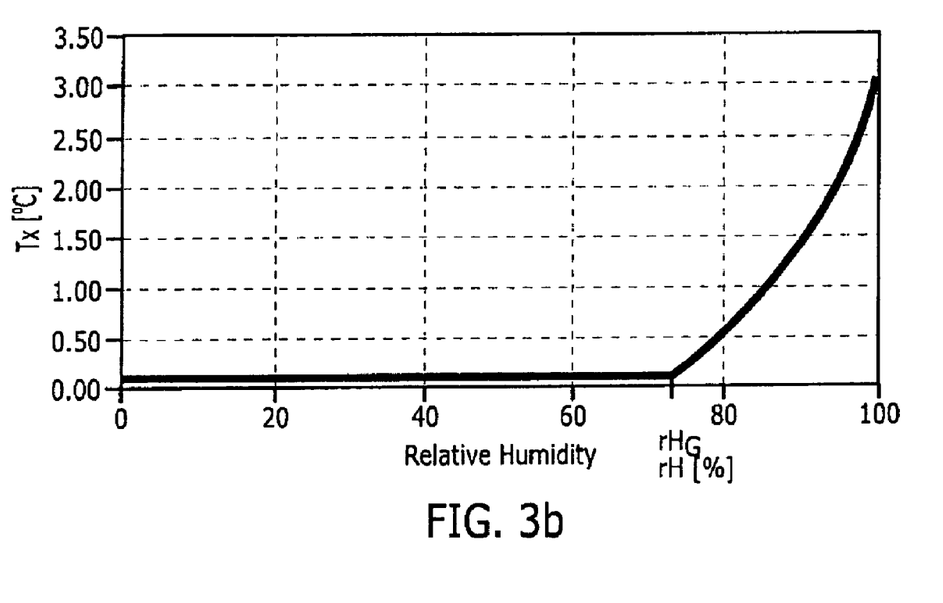
Figure 3C:
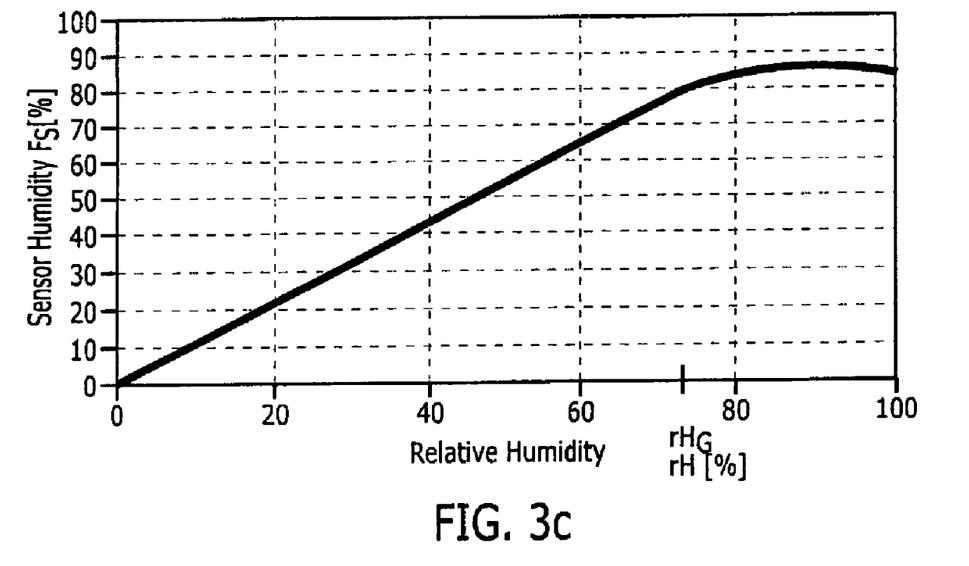

An example embodiment of the heating mode is explained with reference to FIGS. 3a to 3c. In this case, the same variables are plotted versus each other in the different diagrams, as illustrated in FIGS. 2a to 2c already mentioned above.

In this example embodiment, an adjustment is not made in heating mode to a constant sensor humidity, i.e., to a constant capacitance of the provided humidity-sensor element, at or above a humidity limit value $rH_G$. In contrast to the example embodiment described above, it is provided that, in heating mode, measurement current I be allowed to linearly increase with specific relative humidity rH at or above a humidity limit value $rH_G=75\%$, up to a maximum humidity rHmax=100%. The intended relationship between measurement current I and relative humidity rH is represented in FIG. 3a. The resulting curve of the heating of the sensor, i.e., the curve of excess temperature $T_x$, as well as sensor humidity $F_s$, versus relative humidity rH is illustrated in FIGS. 3b and 3c.

In the case of such an example embodiment of the heating mode, decreased expenditure may result, since, for example, no device for regulating the heating current may be necessary on the part of the circuit.

A third option for refining the heating mode is explained with reference to FIGS. 4a to 4c. In the different diagrams, the same variables are plotted versus each other, as in the previous diagrams.

Figure 4A:
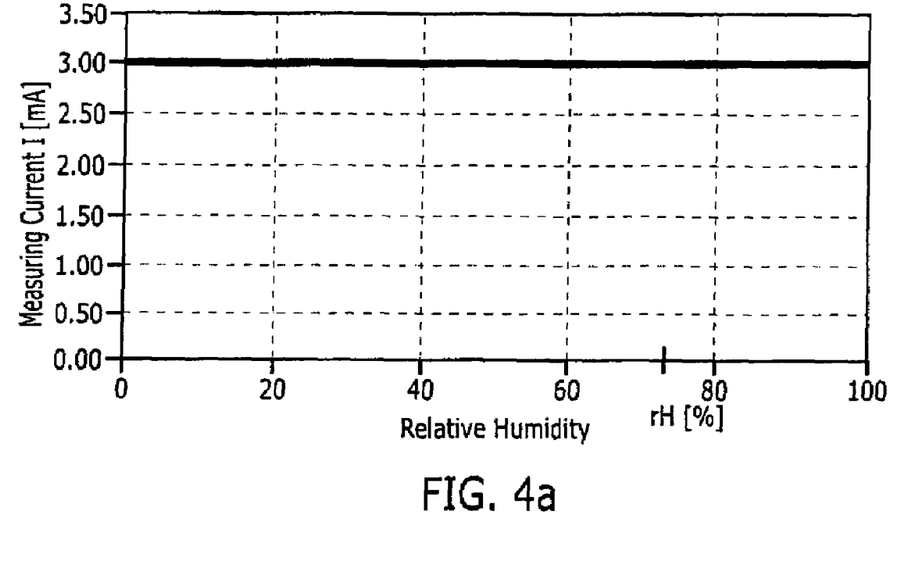
FIGS. 4a to 4c are various diagrams for explaining an example embodiment of the method according to the present invention.
Figure 4B:
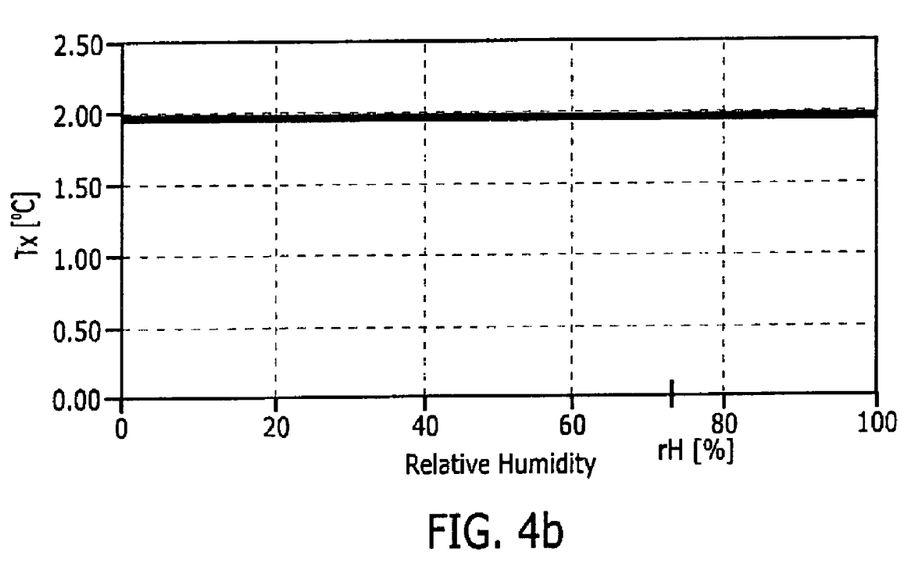
Figure 4C:
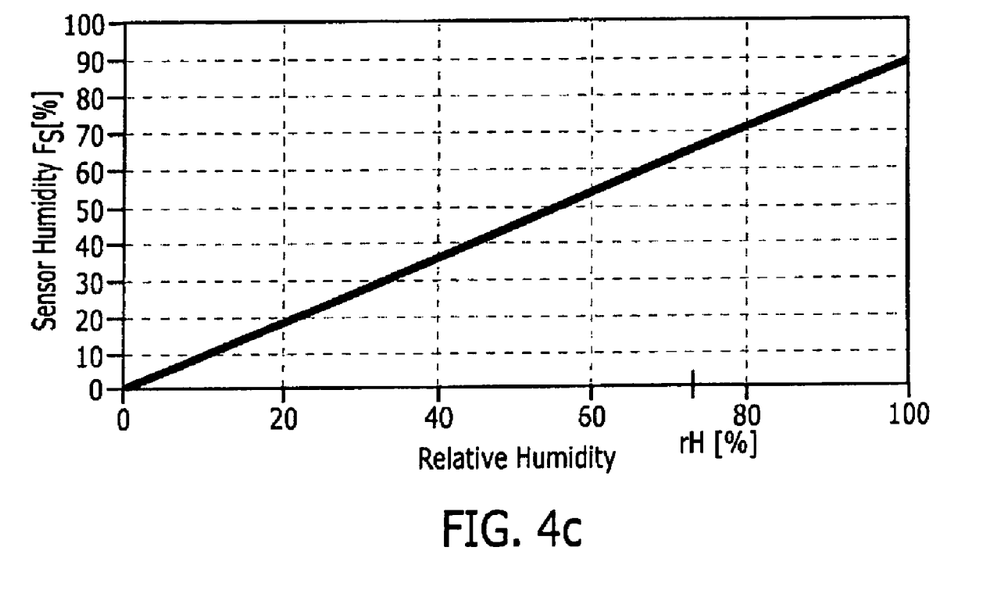

It may be provided that the sensor device is heated over the entire humidity measuring range in an unregulated manner, holding measurement current I constant, as illustrated in FIG. 4a. The corresponding result is a constant excess temperature $T_x$, of the sensor device, as illustrated in FIG. 4b, as well as a sensor humidity $F_s$ as illustrated in FIG. 4c, which increases linearly over the entire humidity measuring range. A reduced total expenditure may be yielded based on this method.

The invention claimed is:

1. A method for measuring humidity by a sensor device including a capacitive humidity-sensor element, a temperature-sensor element, and a heating element, comprising:
   heating the humidity-sensor element in at least a part of a humidity-measuring range;
   ascertaining an ambient temperature by a circuit from a heating power required in the heating step and from a measured local sensor device temperature; and
   determining the relative humidity from the ambient temperature and the local sensor device temperature.

2. The method according to claim 1, wherein the relative humidity is in a range greater than 75% relative humidity.

3. The method according to claim 1, wherein the humidity-sensor element is heated in the heating step over an entire humidity-measuring range.

4. The method according to claim 1, wherein the temperature-sensor element and the heating element are integral.

5. The method according to claim 1, further comprising determining an excess temperature of the heating element resulting from the heating power, the ambient temperature ascertained in the ambient temperature ascertaining step from the heating power and the local sensor device temperature in accordance with the relationship $T_a=T_s-T_x$, $T_a$ representing the ambient temperature, $T_s$ representing the local sensor device temperature and $T_x$ representing the excess temperature.

6. The method according to claim 5, wherein the excess temperature determining step includes determining a corresponding measurement current by the temperature-sensor element, the excess temperature determined in the determining step in accordance with the relationship $T_x = (R \ast TK \ast I^2 \ast EK)$; $T_x$ representing the excess temperature; R representing a measured resistance of the temperature-sensor element; TK representing a temperature coefficient of the temperature-sensor element; I representing the measurement current through the temperature-sensor element; and EK representing a characteristic heating coefficient of the temperature-sensor element.

7. The method according to claim 1, wherein the humidity-sensor element heating step, the ambient temperature ascertaining step and the relative humidity determining step are performed by the circuit connected to the sensor device.

8. The method according to claim 7, wherein the circuit is configured to output the ambient temperature and the relative humidity for further processing.

9. The method according to claim 1, further comprising entering a heating mode at or above a predetermined humidity limit value.

10. The method according to claim 9, wherein the humidity-sensor element is heated in the heating mode in a regulated manner to provide a constant capacitance of the humidity-sensor element.

11. The method according to claim 9, wherein the humidity-sensor element is heated in the heating mode by a heating current that increases linearly with the relative humidity.

12. A device for measuring humidity, comprising:
   a sensor device including a capacitive humidity-sensor element, a temperature-sensor element and a heating element; and
   a circuit configured to heat the humidity-sensor element in at least a part of a humidity-measurement range, and configured to ascertain an ambient temperature from a heating power required in a heating mode and from a measured local sensor device temperature to determine the relative humidity.

13. The device according to claim 12, wherein the device is configured to determine relative humidity in a range greater than 75% relative humidity.

14. The device according to claim 12, wherein the circuit is configured to heat the humidity-sensor element over an entire humidity-measuring range.

15. The device according to claim 12, wherein the temperature-sensor element and the heating element are integral.

16. The device according to claim 12, wherein the temperature-sensor element includes at least one resistor element, the sensor device including a carrier substrate, the capacitive humidity-sensor element and the at lest one resistor element arranged on the carrier substrate.

17. The device according to claim 16, wherein the at least one resistor element is further arranged as the heating element.

18. The device according to claim 12, wherein the circuit is connected to the sensor device and includes at least one microprocessor configured to heat the humidity-sensor element, to perform signal processing and to provide output signals.

19. The device according to claim 12, wherein the circuit is configured to operate the sensor device in the heating mode at or above a predetermined humidity limit value.

20. The device according to claim 19, wherein the circuit is configured to heat, in the heating mode, the humidity-sensor element in a regulated manner to result in a constant capacitance of the humidity-sensor element.

21. The device according to claim 19, wherein the circuit is configured to heat, in the heating mode, the humidity-sensor element by a heating current that increases linearly with the relative humidity.

* * * * *